United States Patent
Moeller et al.

[11] Patent Number: 5,973,781
[45] Date of Patent: Oct. 26, 1999

[54] INTERFEROMETRIC ARRANGEMENT FOR SCANNING AN OBJECT

[75] Inventors: Beate Moeller, Kleinpuerschuetz; Guenter Rudolph, Jena, both of Germany

[73] Assignee: Carl Zeiss Jena GmbH, Jena, Germany

[21] Appl. No.: 09/021,073

[22] Filed: Feb. 9, 1998

[30] Foreign Application Priority Data

Feb. 7, 1997 [DE] Germany .................. 197 04 602

[51] Int. Cl.$^6$ ........................................ G01B 9/02
[52] U.S. Cl. .................. 356/345; 356/351; 356/354; 356/357
[58] Field of Search .................. 356/345, 354, 356/351, 357

[56] References Cited

U.S. PATENT DOCUMENTS

| | | | |
|---|---|---|---|
| 5,353,073 | 10/1994 | Kobayashi | 351/221 |
| 5,719,673 | 2/1998 | Dorsel et al. | 356/345 |
| 5,877,856 | 3/1999 | Fercher | 356/345 |

Primary Examiner—Robert H. Kim
Assistant Examiner—Andrew H. Lee
Attorney, Agent, or Firm—McAulay Nissen Goldberg Kiel & Hand, LLP

[57] ABSTRACT

An interferometric arrangement for scanning an object with an illumination beam path comprises a diffractive optical element (DOE) for generating differently directed beam components of the illuminating light. The DOE is arranged in the illumination beam path in front of at least one scanning element deflecting the illuminating light in at least one direction.

9 Claims, 3 Drawing Sheets

INTERFEROMETRIC ARRANGEMENT FOR SCANNING AN OBJECT

BACKGROUND OF THE INVENTION a) Field of the Invention

A process and a device are known from U.S. Pat. No. 5,321,501, wherein a scanning of an object, preferably an eye, is realized by means of a short-coherence light source and an interferometric beam path with an adjustable reflector in a reference beam path. This enables the detection of interferences or fringes between beam components which are reflected or scattered at layers of various depths and of light reflected in the reference beam path.

A problem consists in this arrangement in that a loss of resolution occurs due to the inevitable, because involuntary, eye movements of the subject, especially axial movements of the eye relative to the instrument, because individual scanned images change their position and can only be correlated with one another again through correlation calculations.

b) Description of the Related Art

In addition to the process and arrangement in the above patent, a scanning laser interferometer for fundus profile measurement was described by Drexler, Hitzenberger, Fercher, and Sattmann in "Conference on Holography and Interferometry in Biomedical Science", Budapest 1993, pages 1–9. Since this arrangement uses the interferences between the light reflected at the fundus and the light reflected at the cornea, axial eye movements are compensated for, but the different divergences of the reflected radiation brings about the problem of a poor signal-to-noise ratio.

Further, arrangements for intraocular distance measurement are also described in DE 3201801, U.S. Pat. No. 5,347,327, U.S. Pat. No. 5,347,328, DE 19624167 A1.

In DE 4446183 A1 by the present Applicant, at least one diffractive optical element (DOE) for dividing the illumination beam path into partial beam paths for different boundary surfaces or interfaces of the eye is provided for intraocular distance measurement, wherein this diffractive optical element is constructed as a type of phase Fresnel lens. The fabrication of micro-Fresnel lenses of this kind is described, for example, in APPLIED OPTICS, Vol. 28, No. 4, Feb. 15, 1989, pages 682–686, and Vol. 29, No. 34, Dec. 1, 1990, pages 5120–5126.

OBJECT AND SUMMARY OF THE INVENTION

It is the primary object of the present invention to realize depth sectional images with high sensitivity independent from the eye movement of the subject.

In accordance with the invention, an interferometric arrangement for scanning an object with an illumination beam path comprises a diffractive optical element (DOE) for generating differently directed beam components of the illuminating light. The DOE is arranged in the illumination beam path in front of at least one scanning element deflecting the illuminating light in at least one direction.

DESCRIPTION OF THE PREFERRED EMBODIMENTS

Figure 1:
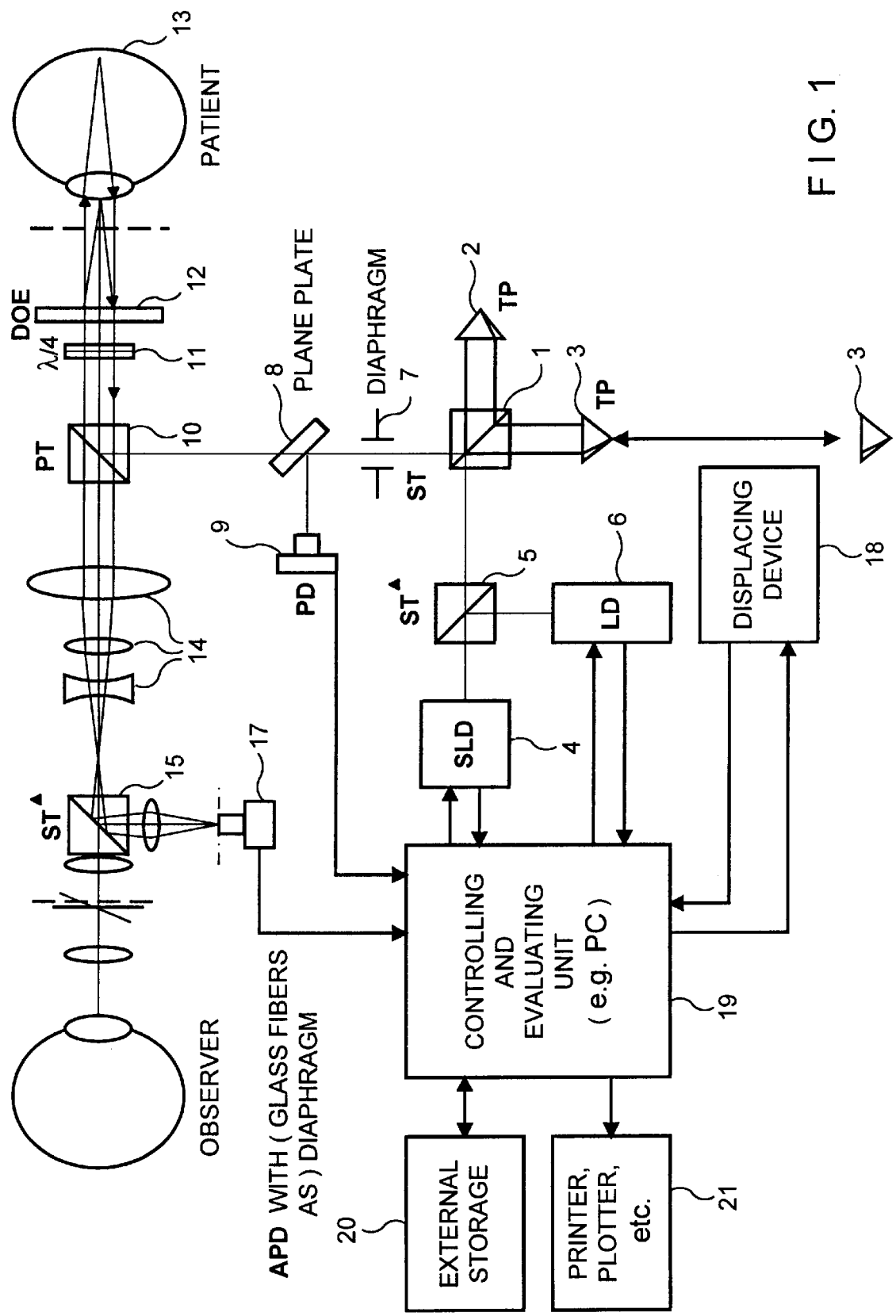
FIG. 1 is an optical schematic showing a known arrangement for intraocular distance measurement.

FIG. 1 shows a known arrangement for intraocular distance measurement comprising a beam splitter 1 with a corner-cube prism 2 and a corner-cube prism 3 which is displaceable by means of a motor and forming an interferometer arrangement into which is radiated the light of a superluminescent diode 4 or laser diode 6, according to preference, serving as measurement light source or as adjustment light source via another beam splitter 5. The advantageously short-coherence illuminating light passes by way of a diaphragm 7 and a plane-parallel plate 8 for blocking out a control component on a photodiode 9 and reaches the eye 13 through a polarizing beam splitter 10, a quarter-wave plate 11 and a DOE 12. A portion of the illuminating light is focussed through the DOE 12 on the corneal vertex, the focal point of the convex corneal mirror or on the center of curvature of the convex corneal mirror, while the other, unaffected parallel beam component is imaged on the retina of the eye via the optics of the eye.

The light which is reflected by the eye and partially collimated by the DOE 12 is imaged via the polarizing beam splitter 10 and a quarter-wave plate and an imaging system 14 via a beam splitter 15 in an observation plane, in which, e.g., the sensor surface of a CCD camera can be arranged, or, as is shown here, on a photodetector 17, preferably an avalanche photodiode. The unused divergent components can be blocked out.

The light sources 4 and 6, a motor-operated displacing device 18 for displacing the corner-cube prism 3, and the photodetectors 9, 17 are coupled with a controlling and evaluating unit 19 which can be connected in turn with external storages 20 and printers 21.

Figure 2:
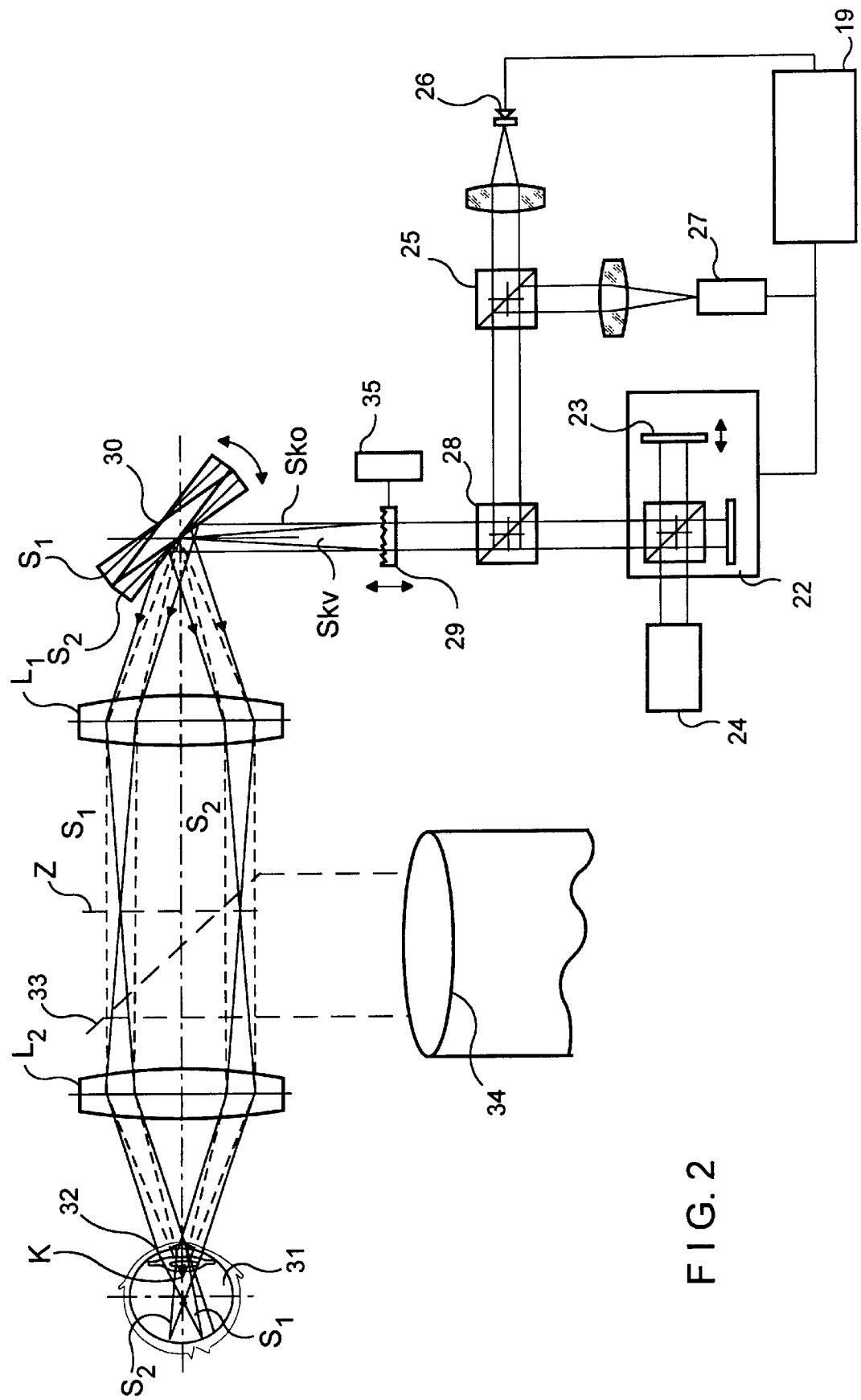
FIG. 2 is an optical schematic of the arrangement of the present invention.

FIG. 2 shows an optical arrangement according to the invention comprising an interferometer 22, shown schematically, with an adjustable reference arm 23 into which is coupled the light of a preferably short-coherence light source 24. A receiver 26 arranged behind the beam splitter 25 serves to detect the measurement light coming back from the eye 31, an adjusting and observation unit 27 serves for monitoring the adjustment of the optical arrangement.

The parallel illuminating light arrives on a DOE 29 constructed as a micro-Fresnel lens via the interferometer arrangement 22 and a pole splitter 28 with quarter-wave plate and is split in a known manner into a collimated beam component Sko and a convergent beam component Skv, wherein the ratio of the beam components Sko, Skv depends on the respective structural configuration of the DOE 29.

The two beam components Sko, Skv arrive at a mirror 30, constructed as a scanner, e.g., a galvo-scanner, and are imaged by the latter so as to be variable in two dimensions in the direction of the eye 31 of the subject via imaging optics which, in the present case, comprise two lenses L1, L2. The first lens L1 generates an intermediate image Z which is imaged on the fundus of the eye by the second lens L2 and by the optics of the eye 31. By means of a sufficiently rapid motor-actuated displacement of the reference mirror 23 in synchronization with the movement of the scanning mirror 30, a depth scan is generated at every position of the scanning mirror 30 enabling the detection of different layers and structures of the eye.

The collimated beam is focussed through the DOE 29 partially on the scanner mirror 30 as a convergent beam component Skv, impinges divergently on lens L1 and travels from the latter as a parallel beam path to lens L2 which generates a beam focus.

In the optical arrangement shown here, this focus is adjusted by means of the adjusting unit 27 in the center of curvature K of the cornea 32 of the eye. The beam component impinging convergently on the surface of the cornea is accordingly reflected divergently and vertically in itself, passes through lenses L2, L1 analogously to the radiating direction and is partially recollimated as it passes through the DOE 29.

The beam component Sko which remains substantially unaffected by the DOE 29 reaches the lens L1 in collimated configuration, wherein the lens L1 generates a focus in an intermediate image plane Z which changes its position corresponding to the position of the scanning mirror 30. This is shown in FIG. 2 by way of example in a first beam path s1 and second beam path s2 which correspond to two different positions S1, S2 of the scanning mirror 30 which lie in a plane.

The second beam component Sko impinges on the front section of the eye via lens L2 as a collimated bundle, is focussed on the retina through the optical action of the eye and is backscattered as a collimated bundle which traverses the lenses L2, L1 analogous to the radiating direction and remains substantially unaffected when passing through the DOE 29.

The point around which the beam impinging on the eye in a parallel manner moves between the scanning positions S1, 82 lies in the focus of the convergent beam component, that is, in the present case, in the center of curvature K of the cornea 32 of the eye. A substantially larger beam component can be used for signal generation by means of beam components from the retina and cornea in the direction of the beam splitter 25 and receiver 26, wherein the beam components are adapted with respect to their wavefronts subsequent to the DOE. The scanner arrangement is simultaneously extensively independent from the movements of the eye.

Figure 3:
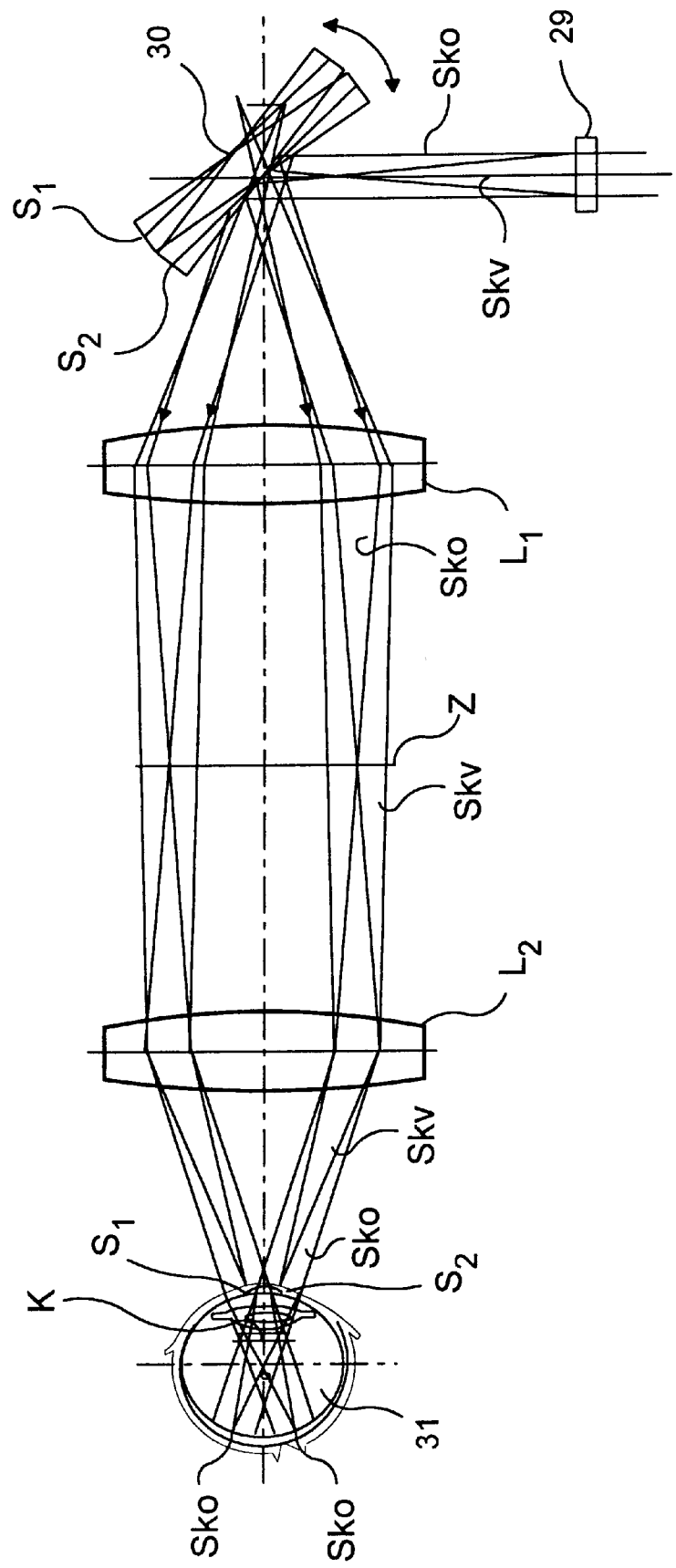
FIG. 3 shows a position of the focus of the convergent beam component on the corneal vertex in two scanning positions.

FIG. 3 shows a position of the focus of the convergent beam component on the corneal vertex in two scanning positions S1, S2, generated by displacement of the DOE 29 in such a way that the focus of the convergent component Skv is arranged in front of the scanning mirror 30.

The focus of the convergent beam component at the eye 31 accordingly moves substantially on the corneal surface on a curved path during the scanning process.

The common center of rotation of the collimated beam components Sko which are offset in S1, S2 lies in the center of curvature K of the cornea of the eye in this case also in a manner analogous to FIG. 2.

The DOE 29 can also be arranged so as to be displaceable axially in order to ensure that the distance between the center of rotation of the collimated component Sko and the focus of the convergent component Skv corresponds precisely to the radius of curvature of the cornea so that the unified reflected beam components can be sufficiently parallel in the direction of the receiver.

For this purpose, the DOE 29 has a displacing unit 35 which, in a manner not shown, is connected with a control unit 19 which is also connected to the adjusting unit 27 and to the interferometer unit 22 as well as to a control unit, not shown, for the scanning mirror 30 for synchronization.

When the DOE 29 is displaced by means of the displacing unit 35, the focussing state can be monitored automatically by means of intensity monitoring by way of receivers 26 and control unit 19.

Further, any vision impairment on the part of the subject can be compensated in an advantageous manner by introducing corrective lenses, not shown, in front of the DOE 29.

FIG. 2 further shows a beam splitter 33 which stops out an observation beam path 34 for observation with ophthalmological instruments such as a fundus camera or a slit lamp. By consulting the resulting intermediate image Z, the physician can accordingly observe the scanning beam and, if required, adjust the scan type scanning direction at the fundus. Conversely, the scanning beam path can also be stopped into an observation beam path.

An advantageous scanning process can be carried out in a second scanning direction either in that the scanning mirror 30 is moved in a second scanning direction enclosing an angle to the first scanning direction or by providing a second scanning mirror. For this purpose, it is necessary to provide the second scanning mirror at the location of the center of rotation of the collimated beam components, wherein a second optical system analogous to lenses L1, L2 then takes over the imaging in the eye.

While the foregoing description and drawings represent the preferred embodiments of the present invention, it will be obvious to those skilled in the art that various changes and modifications may be made therein without departing from the true spirit and scope of the present invention.

What is claimed is:

1. An interferometric arrangement for scanning an eye with illuminating light, comprising:
   an interferometer into which the illuminating light is coupled, said interferometer having at least one adjustable interferometer arm for adjusting an optical path length difference;
   a diffractive optical element (DOE) for receiving illuminating light output from said interferometer and for generating differently directed beam components of the illuminating light; and
   at least one scanning element for deflecting in at least one direction the differently directed beam components of the illuminating light;
   said interferometric arrangement being adapted to detect different layers and structures in the eye from the beam components reflected from the eye.

2. A method for scanning an eye with an illuminating light, comprising the steps of:
   generating differently directed beam components of the illuminating light by a diffractive optical element (DOE);
   deflecting the differently directed beam components of the illuminating light in at least one direction by at least one scanning element; and
   detecting different layers and structures in the eye from the beam components reflected from the eye.

3. The arrangement according to claim 1, wherein the DOE has a partially funnelling or collecting effect on incident illuminating light.

4. The arrangement according to claim 1, wherein the DOE is constructed as a micro-Fresnel lens.

5. The arrangement according to claim 1, wherein imaging optics are provided between the scanning element and the eye for providing the differently directed beam components to the eye.

6. The arrangement according to claim 1, wherein an observation beam path is stopped out between the scanning element and the eye.

7. The arrangement according to claim 1, wherein at least one convergent and one collimated illumination component is generated through the DOE.

8. The arrangement according to claim 7, wherein the convergent illumination component is imaged on the cornea of the eye or on the center of curvature of the cornea of the eye.

9. The arrangement according to claim 1, wherein said at least one scanning element is at least one scanning mirror that is adjustable in at least one direction.

* * * * *